(12) United States Patent
Bublewitz et al.

(10) Patent No.: US 7,681,762 B2
(45) Date of Patent: Mar. 23, 2010

(54) DEVICE FOR STORING AND DISPENSING FLUID SUBSTANCES

(75) Inventors: Alexander Bublewitz, Herborn (DE); Matthias Suchan, Herborn (DE)

(73) Assignee: Kettenbach GmbH & Co. KG, Eschenburg (DE)

( * ) Notice: Subject to any disclaimer, the term of this patent is extended or adjusted under 35 U.S.C. 154(b) by 940 days.

(21) Appl. No.: 11/335,447

(22) Filed: Jan. 19, 2006

(65) Prior Publication Data

US 2006/0157503 A1  Jul. 20, 2006

(30) Foreign Application Priority Data

Jan. 20, 2005  (DE)  .................. 20 2005 000 929 U

(51) Int. Cl.
 *B65D 35/22*  (2006.01)
(52) U.S. Cl. .................. 222/153.09; 222/94; 222/105; 222/137; 222/153.1; 222/325
(58) Field of Classification Search .................. 222/94, 222/153.09, 137, 145.6, 153.1, 153.01, 105, 222/135, 145.5, 325–327, 391
See application file for complete search history.

(56) References Cited

U.S. PATENT DOCUMENTS

| | | | | |
|---|---|---|---|---|
| 1,279,077 A | * | 9/1918 | Bohlman | .................. 222/131 |
| 4,753,536 A | * | 6/1988 | Spehar et al. | ............... 366/339 |
| 5,398,846 A | | 3/1995 | Corba et al. | |
| 6,352,177 B1 | | 3/2002 | Bublewitz et al. | |
| 6,394,643 B1 | | 5/2002 | Bublewitz et al. | |

FOREIGN PATENT DOCUMENTS

| | | |
|---|---|---|
| DE | 79 34 536.1 | 12/1979 |
| DE | 100 38 882 | 4/2001 |
| DE | 299 23 938 | 8/2001 |
| DE | 695 30 629 | 10/2003 |
| EP | 1 125 641 | 5/2003 |
| WO | WO 00/21653 | 4/2000 |

OTHER PUBLICATIONS

Office Action of German Patent Office (w/translation).

* cited by examiner

*Primary Examiner*—J. Casimer Jacyna
(74) *Attorney, Agent, or Firm*—Collard & Roe, P.C.

(57) ABSTRACT

A device for storing and dispensing fluid substances has at least one container for accommodating fluid substances, at least one outlet tap that is provided on the face of the container, a dispensing element that can be connected with the outlet tap, and a locking element for releasably locking the dispensing element on the outlet tap(s). A guide is provided on the container, in which the locking element is guided in such a manner that it can be transferred, perpendicular to the longitudinal axis of the container, from a first open position in which the dispensing element is released, into a second locking position, in which it surrounds the dispensing element at least in part, to fix it in place on the at least one outlet tap.

11 Claims, 4 Drawing Sheets

DEVICE FOR STORING AND DISPENSING FLUID SUBSTANCES

BACKGROUND OF THE INVENTION

1. Field of the Invention

The invention relates to a device for storing and dispensing fluid substances, which has at least one container, particularly a cylindrical container, for accommodating fluid substances, at least one outlet tap that is provided on the face of the container, a dispensing element that can be connected with the outlet tap, and a locking element for releasably locking the dispensing element on the outlet tap(s).

2. The Prior Art

Double cartridges or double syringes formed from two cylinders are known for storing and dispensing fluid substances from which multi-component materials can be mixed, in which the fluid substances are stored separate from one another. This is often used in dental preparations. Before use, these substances are dispensed from the device by a dispensing element, and mixed with one another, causing the substances to react with one another and cure. In many cases, an amount of the fluid substances that is sufficient for several applications is stored in the double cartridges or double syringes. The dispensing elements, which can be a static or dynamic mixer, for example, are therefore mostly disposable articles that must be attached to the container for use and afterwards must be removable from it, to dispose of them.

A device for dispensing a mixed multi-component mass is described in German Patent No. DE 100 38 882 A1, which device has containers having outlet taps as well as a coupling plate carried on them. The latter forms a guide for a frame-like coupling slide with which a mixer can be covered, in certain regions.

Particularly when the mixers are changed, residues of the components to be mixed with one another can remain on the coupling plate. There is therefore the risk that the components to be mixed contact one another and react even before they reach the mixer. This results in clogging of the outlet taps, making the entire device no longer usable.

Double cartridges formed from two cylinders connected with one another are known, in which each outlet tap can be releasably closed off via caps. In order to fix the caps in place on the cylinders, as well as in order to fix a mixer or the like in place on the outlet taps, a pivoting bracket is provided on a crosspiece that connects the cylinders with one another, on the side facing away from the caps, in the case of these known double cartridges. This bracket can be locked in place in a position oriented parallel to the cylinders, for example with a snap closure, in which position one end of the bracket holds the caps and the mixer in place. In order to allow the bracket to pivot open, however, too much construction space is required in some cases.

SUMMARY OF THE INVENTION

It is therefore an object of the present invention to develop a two-chamber dispensing device in which a dispensing element can be attached to a container in simple and secure manner, and released from it again.

This is achieved, according to the invention, by providing a guide on the container, in which the locking element is guided in such a manner that it can be transferred, perpendicular to the longitudinal axis of the container, from a first open position in which the dispensing element is released, into a second locking position, in which it surrounds the dispensing element at least in part, to fix it in place on the at least one outlet tap.

In the open position, a dispensing element can be set onto the container or removed from it, without the locking element preventing this. In contrast, when the locking element has been transferred from its open position into the locking position, it is brought into contact with the dispensing element in such a manner that even under great press-out pressure of the fluid substances, the dispensing element is reliably prevented from unintentionally falling off.

If a single-component system is stored and/or dispensed with the device according to the invention, the container can be formed by only one cylinder or the like. However, impression masses for the dental sector are frequently mixed from two-component or multi-component systems. In this connection, it is preferred if the container is a double cartridge or a double syringe, formed, for example, by two cylinders connected with one another by way of at least one crosspiece, on which double cartridge or double syringe two outlet taps are provided. However, the form of the container is not limited to two cylinders that are oriented parallel to one another and connected with one another at their sides. Instead, the cylinders or the like can also be disposed coaxially within one another, for example, whereby a smaller cylinder is accommodated in a larger cylinder.

Furthermore, the container(s) can also have a non-cylindrical shape. The term "cylinder" is therefore being used here only as an example for a possible shape of the containers.

Preferably, the guide is formed by at least one slot in the crosspiece, by means of which the cylinders are connected with one another, which slot runs essentially parallel to the longitudinal axes of the cylinders. Alternatively, a projection, particularly an elongated projection, can project away from the crosspiece, and be connected with the locking element. This can take place, for example, by means of two spring legs having hook-like ends, onto which the locking element can be engaged with a corresponding slot-like recess. In the case of these configurations with a guide disposed on or at the crosspiece, the inside contour of the cylinders is not influenced thereby.

The locking element can have a guide segment that runs at least essentially parallel to the longitudinal axis of the at least one container, and a holding segment that runs perpendicular to the longitudinal axis of the at least one container. In this connection, a handle can be provided on the guide segment, so that the locking element can be seized and activated well. This allows one-handed operation of the device according to the invention.

According to a preferred embodiment of the invention, the holding segment of the locking element is configured in U shape, to surround the dispensing element. Alternatively, the holding segment can also be configured in a semi-circular shape, for example, with arc-shaped crosspieces for surrounding the dispensing element. In order to achieve defined positioning of the locking element in its locking position, at least one recess can furthermore be provided on the holding segment, for contact against the at least one outlet tap.

Preferably, the container has at least one cylinder directly filled with the fluid substances. Alternatively to this, tubular bags or the like can also be filled into each cylinder of the container, in which the fluid substances are accommodated. The cylinders can therefore be used once or multiple times. The use of such tubular bags can also be advantageous if insufficient storage stability can be achieved when the fluid substances are stored directly in the cylinders.

In this connection, it has proven to be particularly advantageous if the tubular bags are attached to the at least one cylinder, for example by means of a glue connection. At the same time, this glue connection can seal the tubular bags relative to the cylinders, so that the tubular bags can be pierced and opened in the cylinders, for example through the outlet taps. In order to prevent exit of the substances during transport and storage, the outlet taps can be closed off with a plug or the like, so that a user merely has to remove the plugs before putting the device according to the invention into operation. At the same time, the pistons that are usually used for closure in the case of directly filled cylinders, which are provided at the back ends of the cylinders, can be eliminated with this configuration of the device according to the invention.

If two-component systems are being stored and/or dispensed in the device according to the invention, the outlet taps are provided on the caps, for example, which firmly close off a face of the cylinder of a double cartridge that forms the container, in each instance. Alternatively to this, the outlet taps can also be provided on two separate caps, or two caps that are rigidly connected with one another, which releasably close off a face of the cylinder of a double cartridge that forms the cylinder, in each instance.

According to another embodiment of the invention, a device having at least two containers that can be joined together to form a double cartridge is provided. The containers form a chamber, in each instance, whereby the chamber walls have different permeability, particularly different air permeability. This can be achieved either by means of different material properties of the chamber walls, or in that one of the chambers is sealed off, particularly with regard to the surroundings, for example by means of a tubular bag that is accommodated in it. The different permeability of the chambers can lower the production costs of a cartridge, on the one hand, if particular sealing requirements are set only for one chamber and, on the other hand, can permit an air exchange or the like with the surroundings, if this is desired in some cases.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views.

DETAILED DESCRIPTION OF THE PREFERRED EMBODIMENT

Figure 1:
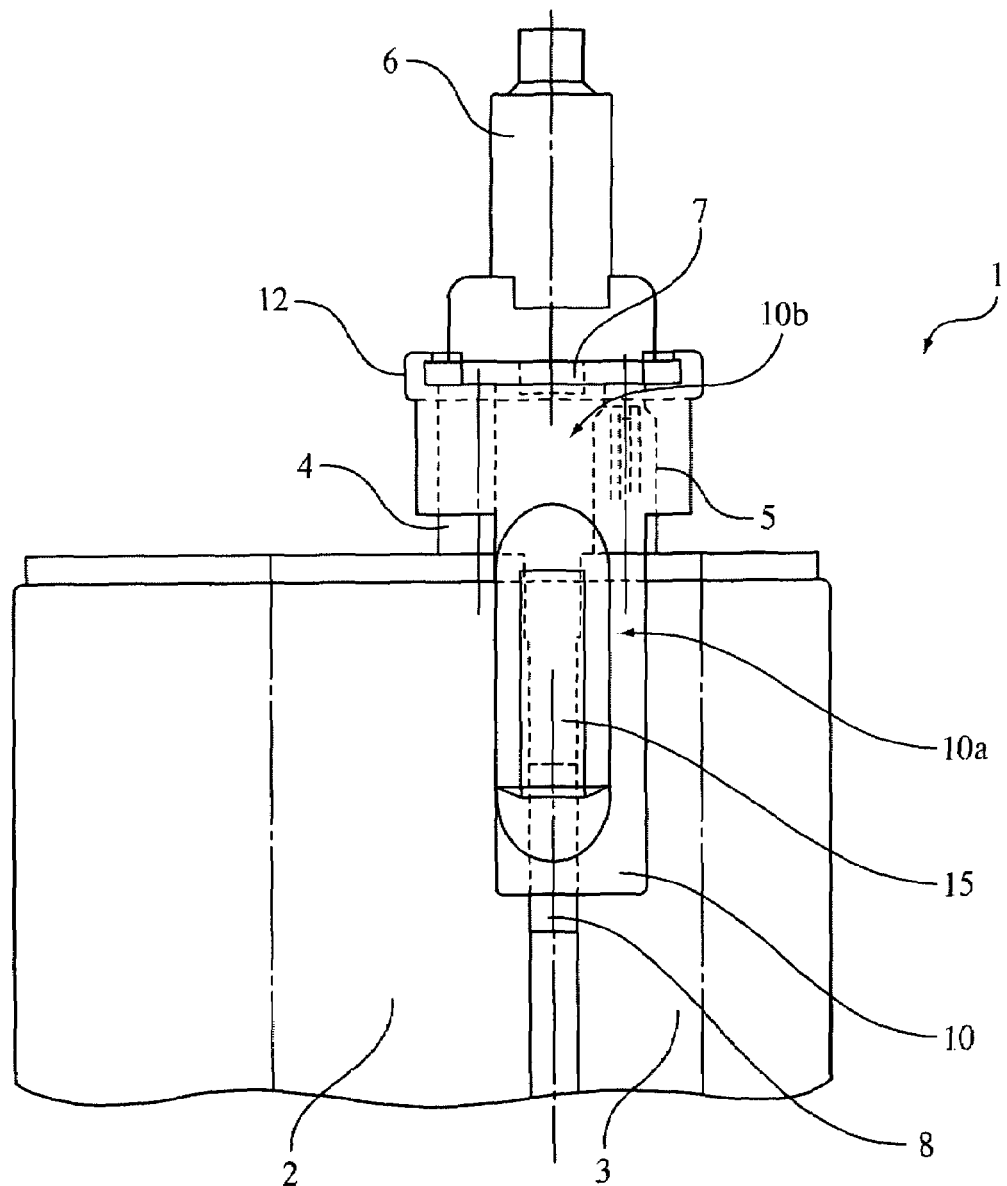
FIG. 1 shows a side view of the device according to the invention.

The device for storing and dispensing fluid substances shown in the figures has a container 1 having two cylinders 2, 3 that form a double cartridge, for accommodating different fluid substances. These substances can either be filled directly into cylinders 2, 3, or accommodated in a tubular bag that is not shown in the drawing, which bag in turn is filled into the cylinder and connected with the inside cylinder wall, particularly with the face of the cylinder.

Each of the two cylinders 2, 3 is provided with an outlet tap 4 or 5, respectively, which projects away from the face of container 1. These outlet taps can be connected with a dispensing element 6, which is a dynamic mixer in the embodiment shown. For this purpose, dispensing element 6 has inlet taps, the size of which is dimensioned in such a manner that they can be inserted into outlet taps 4, 5 of container 1, or vice versa. Furthermore, dispensing element 6 is provided with a flange-like edge 7 on its end that faces container 1 in FIG. 1, on which the inlet taps are also provided.

In the embodiment shown in FIG. 1, a crosspiece 8 is provided between the two cylinders 2, 3, which connects the two cylinders. Two spring legs 9 having hook-like ends project away from crosspiece 8. In this connection, these spring legs 9 form a projection that extends parallel to the longitudinal axes of the two cylinders.

Figure 2:
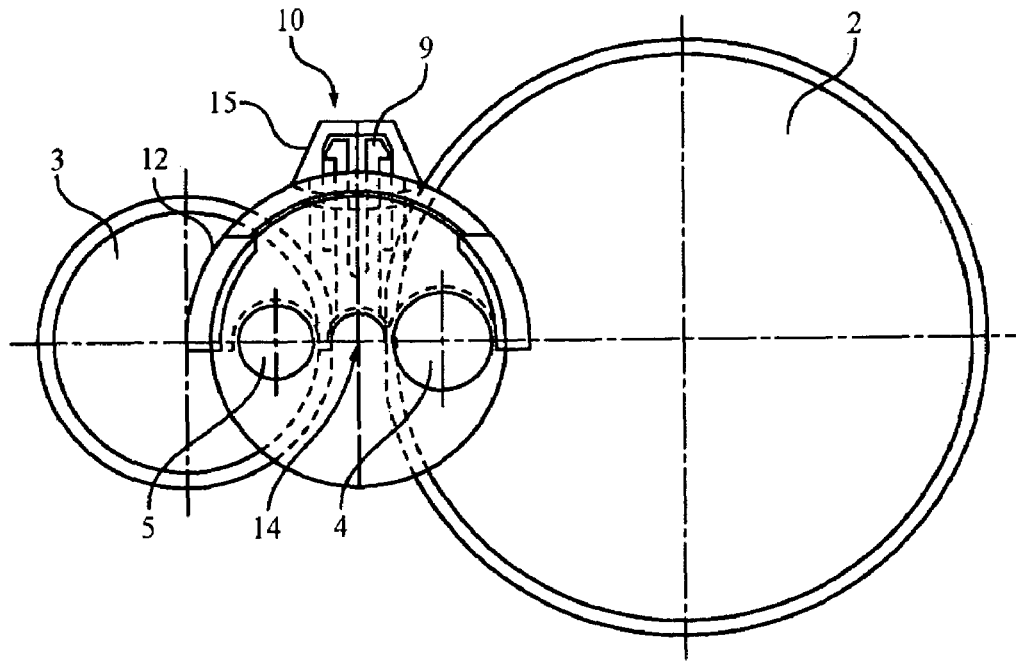
FIG. 2 shows a top view of the locking element from FIG. 1, in its locking position.
Figure 3:
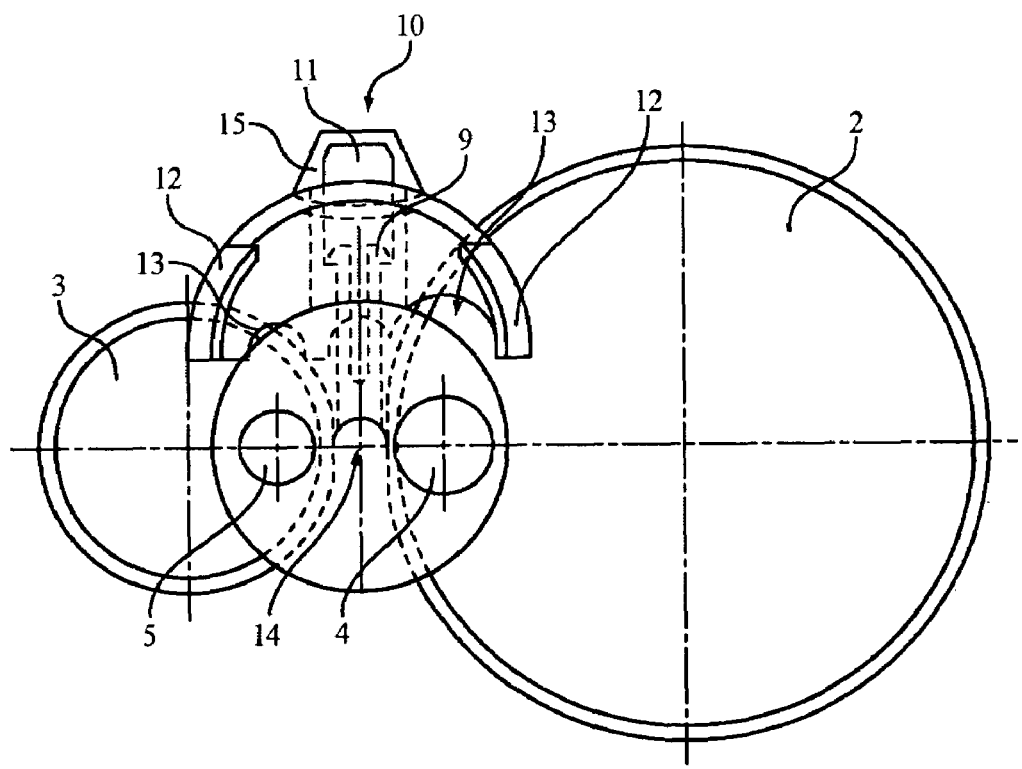
FIG. 3 shows a top view of the locking element from FIG. 1, in its open position.
Figure 4:
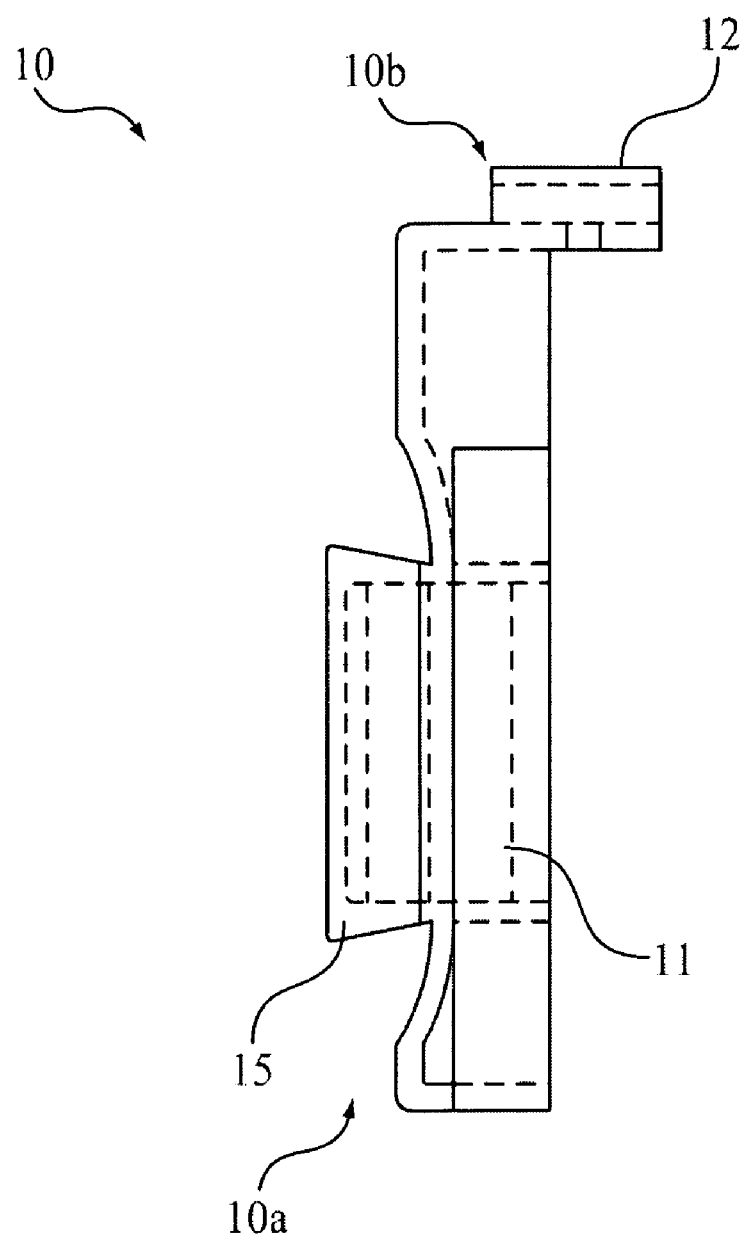
FIG. 4 shows a side view of the locking element from FIG. 1.

A locking element 10 shown in FIG. 4 has a slot-like recess 11 in a guide segment 10a, which recess is dimensioned in such a manner that locking element 10 can be engaged onto the spring legs 9 and displaced on them. In this connection, the spring legs serve as a guide on which locking element 10 can be moved in a direction perpendicular to the longitudinal axes of the cylinders 2, 3, between a locking position shown in FIG. 2, in which locking element 10 is displaced towards the crosspiece 8, and an open position shown in FIG. 3, in which locking element 10 is removed from the crosspiece 8. Locking element 10 is held on the spring legs so that it cannot come off, by means of the hook-like ends of spring legs 9.

A holding segment 10b is disposed on locking element 10 in one piece with lower guide segment 10a shown in FIG. 1, which former segment extends perpendicular to longitudinal axes of the cylinders 2, 3. In the embodiment shown, holding segment 10b is formed by a semi-circular plate, which has two arc-shaped crosspieces 12 for surrounding flange-like edge 7 of mixer 6. Furthermore, recesses 13 are provided in the plate of the holding segment 10b, which are dimensioned in such a manner that they rest against outlet taps 4 and 5 in order to limit the movement of locking element 10 in the locking position. A further recess 14 disposed between these recesses 13 serves to pass through a shaft that drives mixer 6, which shaft is not shown in the figures.

In the open position, dispensing element 6 can be set onto or pulled off from outlet taps 4, 5, without touching the locking element 10. On the other hand, when locking element 10 is pushed from its open position, shown in FIG. 3, into the locking position, the arc-shaped crosspieces 12 of locking element 10, which surround flange-like edge 7, prevent the dispensing element 6 from being pulled off from outlet taps 4, 5.

For easier activation of the locking element 10, a handle 15 is provided on the side that faces away from slot-like recess 11. In this connection, the cavity of slot-like recess 11 for accommodating spring legs 9 can extend into handle 15.

In deviation from the representation in FIG. 1, the locking element 10 according to the invention can be used not only for double cartridges, but also for individual containers for accommodating single-component systems. Furthermore, it is also possible to dispose cylinders 2, 3 not parallel next to one another, but to accommodate the smaller cylinder in a larger cylinder, for example coaxially. Locking element 10 is then provided in the outside wall of the larger or individual cylinder.

Figure 5:
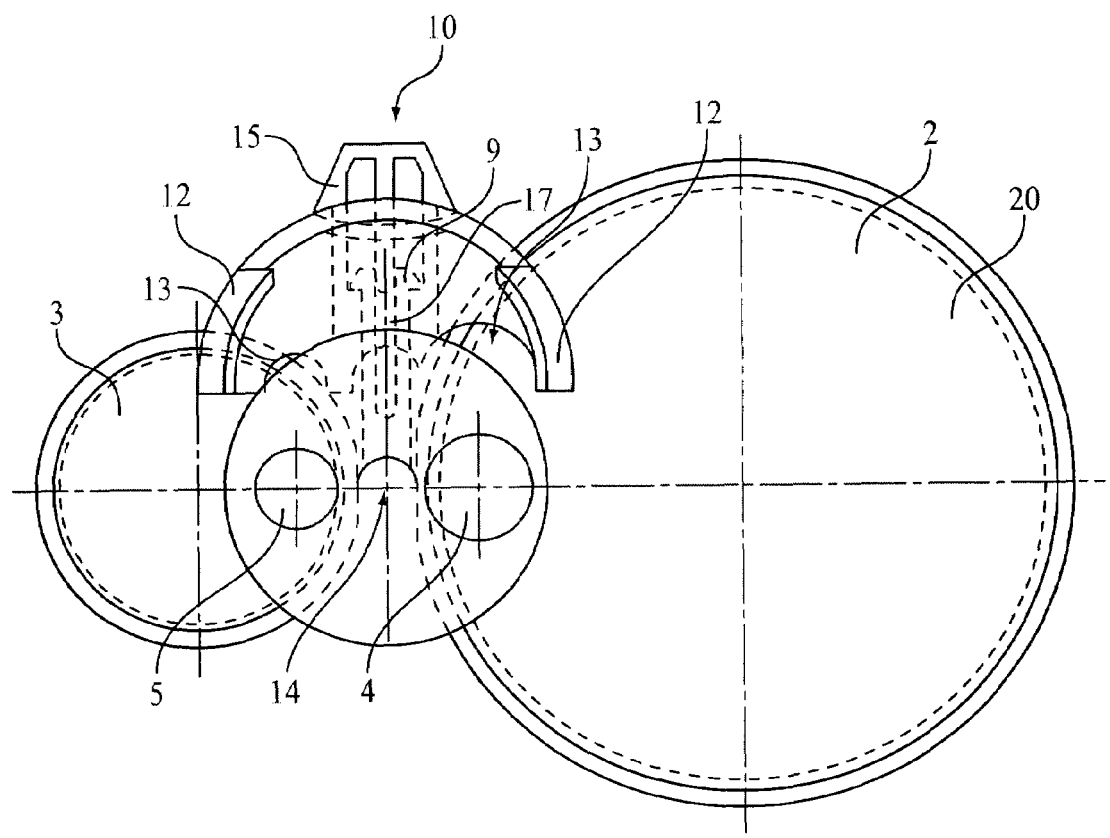
FIG. 5 shows a top view of an alternative embodiment of the locking element according to the invention.

FIG. 5 shows an alternative embodiment of the locking element, where cylinders 2, 3 are connected to each other via a slot 17 in crosspiece. The fluid substances are disposed inside tubular bags 20 which are placed inside containers 2, 3, and can be sealed there.

Accordingly, while only a few embodiments of the present invention have been shown and described, it is obvious that many changes and modifications may be made thereunto without departing from the spirit and scope of the invention.

REFERENCE SYMBOL LIST 1 container
2 cylinder
3 cylinder
4 outlet tap
5 outlet tap
6 dispensing element
7 flange-like edge
8 crosspiece
9 spring leg (guide)
10 locking element
10a guide segment
10b holding segment
11 slot-like recess
12 arc-shaped crosspiece
13 recess
14 recess
15 handle
17 slot
20 tubular bag

What is claimed is:

1. A device for storing and dispensing fluid substances, comprising:
   at least one container for accommodating fluid substances;
   at least one outlet tap disposed on a face of the container;
   a dispensing element adapted to be connected with the outlet tap;
   a guide disposed on the container; and
   a locking element for releasably locking the dispensing element on the outlet tap, said locking element being guided in the guide so that the locking element moves, perpendicular to a longitudinal axis of the container, from a first open position in which the dispensing element is released, into a second locking position, in which the locking element surrounds the dispensing element at least in part, to fix the dispensing element in place on the at least one outlet tap, the locking element being guided in the guide both in the first open position and in the second locking position,
   wherein the container is a double cartridge having two cylinders connected with one another by at least one crosspiece, and wherein there are two outlet taps, and wherein the dispensing element is a mixer, which has two inlet taps that are complementary to the outlet taps, at least in certain regions, and has a flange-like edge located on a side of the mixer having the inlet taps, with which edge the locking elements are brought into engagement.

2. A device according to claim 1, wherein the guide is formed by at least one slot in the crosspiece, wherein the cylinders are connected with one another via the slot, the slot running essentially parallel to longitudinal axes of the cylinders.

3. A device according to claim 1, wherein the guide is formed by at least one projection that runs parallel to longitudinal axes of the cylinders.

4. A device according to claim 3, wherein the at least one projection comprises two spring legs that engage in the locking element, on the crosspiece that connects the cylinders.

5. A device according to claim 1, wherein the locking element has a guide segment that runs at least essentially parallel to the longitudinal axis of the at least one container, and a holding segment that runs at least essentially perpendicular to the longitudinal axis of the at least one container.

6. A device according to claim 5, further comprising a handle on the guide segment of the locking element.

7. A device according to claim 1, wherein the container has at least one cylinder directly filled with the fluid substances.

8. A device for storing and dispensing fluid substances, comprising:
   at least one container for accommodating fluid substances;
   at least one outlet tap disposed on a face of the container;
   a dispensing element adapted to be connected with the outlet tap;
   a guide disposed on the container; and
   a locking element for releasably locking the dispensing element on the outlet tap, said locking element being guided in the guide so that the locking element moves, perpendicular to a longitudinal axis of the container, from a first open position in which the dispensing element is released, into a second locking position, in which the locking element surrounds the dispensing element at least in part, to fix the dispensing element in place on the at least one outlet tap, the locking element being guided in the guide both in the first open position and in the second locking position,
   wherein the locking element has a guide segment that runs at least essentially parallel to the longitudinal axis of the at least one container, and a holding segment that runs at least essentially perpendicular to the longitudinal axis of the at least one container,
   wherein the holding segment of the locking element is configured in U shape, to surround the dispensing element.

9. A device for storing and dispensing fluid substances, comprising:
   at least one container for accommodating fluid substances;
   at least one outlet tap disposed on a face of the container;
   a dispensing element adapted to be connected with the outlet tap;
   a guide disposed on the container; and
   a locking element for releasably locking the dispensing element on the outlet tap, said locking element being guided in the guide so that the locking element moves, perpendicular to a longitudinal axis of the container, from a first open position in which the dispensing element is released, into a second locking position, in which the locking element surrounds the dispensing element at least in part, to fix the dispensing element in place on the at least one outlet tap, the locking element being guided in the guide both in the first open position and in the second locking position,
   wherein the locking element has a guide segment that runs at least essentially parallel to the longitudinal axis of the at least one container, and a holding segment that runs at least essentially perpendicular to the longitudinal axis of the at least one container,
   wherein the holding segment of the locking element has arc-shaped crosspieces for surrounding the dispensing element, and further comprising at least one recess for resting against the at least one outlet tap.

10. A device for storing and dispensing fluid substances, comprising:

at least one container for accommodating fluid substances;
at least one outlet tap disposed on a face of the container;
a dispensing element adapted to be connected with the outlet tap;
a guide disposed on the container; and
a locking element for releasably locking the dispensing element on the outlet tap, said locking element being guided in the guide so that the locking element moves, perpendicular to a longitudinal axis of the container, from a first open position in which the dispensing element is released, into a second locking position, in which the locking element surrounds the dispensing element at least in part, to fix the dispensing element in place on the at least one outlet tap, the locking element being guided in the guide both in the first open position and in the second locking position,
wherein the container has at least one cylinder filled with tubular bags in which the fluid substances are accommodated, wherein the tubular bags are attached to the at least one cylinder, forming a seal.

11. A device for storing and dispensing fluid substances, comprising:

at least one container for accommodating fluid substances;
at least one outlet tap disposed on a face of the container;
a dispensing element adapted to be connected with the outlet tap;
a guide disposed on the container; and
a locking element for releasably locking the dispensing element on the outlet tap, said locking element being guided in the guide so that the locking element moves, perpendicular to a longitudinal axis of the container, from a first open position in which the dispensing element is released, into a second locking position, in which the locking element surrounds the dispensing element at least in part, to fix the dispensing element in place on the at least one outlet tap, the locking element being guided in the guide both in the first open position and in the second locking position,
wherein there are two containers forming a double cartridge, and wherein walls of the container have different permeability from each other.

* * * * *